US012595109B2

(12) United States Patent  
Becker

(10) Patent No.: US 12,595,109 B2  
(45) Date of Patent: Apr. 7, 2026

(54) DEVICE TO RELEASE WATER AND ANTIMICROBIAL VAPOR INTO AN ENCLOSED OR PARTIALLY ENCLOSED SPACE

(71) Applicant: Arkema Inc., King of Prussia, PA (US)

(72) Inventor: Christian G. Becker, King of Prussia, PA (US)

(73) Assignee: Arkema Inc., King of Prussia, PA (US)

( * ) Notice: Subject to any disclaimer, the term of this patent is extended or adjusted under 35 U.S.C. 154(b) by 598 days.

(21) Appl. No.: 17/913,266

(22) PCT Filed: Mar. 4, 2021

(86) PCT No.: PCT/US2021/020814  
§ 371 (c)(1),  
(2) Date: Sep. 21, 2022

(87) PCT Pub. No.: WO2021/194713  
PCT Pub. Date: Sep. 30, 2021

(65) Prior Publication Data

US 2023/0146660 A1     May 11, 2023

Related U.S. Application Data

(60) Provisional application No. 63/000,556, filed on Mar. 27, 2020.

(51) Int. Cl.

| | |
|---|---|
| *A61L 9/00* | (2006.01) |
| *A23B 2/712* | (2025.01) |
| *A23B 7/144* | (2006.01) |
| *A61L 2/00* | (2006.01) |
| *A61L 2/208* | (2026.01) |
| *A61L 2/26* | (2006.01) |
| *B01J 20/10* | (2006.01) |
| *B01J 20/26* | (2006.01) |
| *B01J 20/28* | (2006.01) |
| *B65B 31/00* | (2006.01) |
| *B65B 55/19* | (2006.01) |
| *B65D 81/24* | (2006.01) |

(52) U.S. Cl.  
CPC .............. *B65D 81/24* (2013.01); *A23B 2/712* (2025.01); *A23B 7/144* (2013.01); *A61L 2/208* (2013.01); *A61L 2/26* (2013.01); *B01J 20/103* (2013.01); *B01J 20/261* (2013.01); *B01J 20/267* (2013.01); *B01J 20/2805* (2013.01); *B65B 55/19* (2013.01)

(58) Field of Classification Search  
CPC .......... B65D 81/24; A23B 2/712; B01J 20/28; A61L 9/00; A61L 9/04; A61L 9/05

USPC ....... 252/187.23; 424/47; 53/434; 422/5, 28, 422/305  
See application file for complete search history.

(56) References Cited

U.S. PATENT DOCUMENTS

| | | | |
|---|---|---|---|
| 4,035,303 A | 7/1977 | Ufferfilge | |
| 4,680,173 A * | 7/1987 | Burger ..................... | C09K 3/30 |
| | | | 424/47 |
| 5,061,258 A | 10/1991 | Martz | |
| 5,091,107 A * | 2/1992 | Hutchings ................. | A61L 2/20 |
| | | | 252/187.23 |
| 8,790,630 B2 | 7/2014 | Abe | |
| 9,358,569 B2 * | 6/2016 | Burt .................... | B05B 17/0615 |
| 9,409,866 B2 | 8/2016 | Grether et al. | |
| 2006/0097223 A1 | 5/2006 | Powers et al. | |
| 2006/0280665 A1 | 12/2006 | Rees et al. | |
| 2015/0190543 A1 * | 7/2015 | Marshall ................. | A61L 15/24 |
| | | | 424/443 |
| 2015/0297861 A1 * | 10/2015 | Passalaqua ............. | B65B 5/045 |
| | | | 53/434 |
| 2017/0217661 A1 | 8/2017 | Erickson | |
| 2018/0289009 A1 | 10/2018 | Lee et al. | |
| 2020/0299621 A1 | 9/2020 | Becker et al. | |

FOREIGN PATENT DOCUMENTS

| | | |
|---|---|---|
| AU | 2006202977 B1 | 3/2007 |
| JP | S6147401 A | 3/1986 |
| JP | H09117270 A | 5/1997 |
| JP | 2016208847 A2 | 12/2016 |
| KR | 101732958 B1 | 5/2017 |
| WO | WO2016123716 A1 | 8/2016 |
| WO | WO2019215764 A1 | 11/2019 |

OTHER PUBLICATIONS

Chlorine Dioxide—Use, Benefits, and Chemical Safety Facts. ChemicalSafetyFacts.org, ChemicalSafetyFacts, Feb. 2, 2020, www.chemicalsafetyfacts.org/chlorine-dioxide/.

* cited by examiner

*Primary Examiner* — Monzer R Chorbaji  
(74) *Attorney, Agent, or Firm* — Debodhonyaa Sengupta

(57) ABSTRACT

Devices and methods for provided both an antimicrobial vapor such as hydrogen peroxide and/or peracetic acid and water vapor in an enclosed or partially enclosed space are described. The device and method provided is for the reduction or elimination of microbes from air and surfaces in contact with air within an enclosed or partially enclosed space using hydrogen peroxide or peracetic acid in the vapor phase and also provide for humidity from water vapor. The device and method are directed towards a release of an antimicrobial vapor and water vapor through a permeable container/barrier containing a matrix into which water and an antimicrobial vapor producing material are absorbed.

27 Claims, No Drawings

DEVICE TO RELEASE WATER AND ANTIMICROBIAL VAPOR INTO AN ENCLOSED OR PARTIALLY ENCLOSED SPACE

This present application is the national phase under 35 USC § 371 of prior PCT International Application Number PCT/US2021/020814 filed Mar. 4, 2021 which designated the United States of America and claimed priority to U.S. Provisional Patent Application Ser. No. 63/000,556 filed Mar. 27, 2020.

FIELD OF THE INVENTION

The present invention relates to a device for treatment of enclosed or partially enclosed space with water vapor and an antimicrobial vapor. Such treatment, for example, can be for the protection of goods prone to damage and spoilage caused by microbes or microorganisms—namely bacteria, archaea, fungi (yeasts and molds), algae, protozoa, and viruses and/or dehydration, such as, for example, produce such as fruits, vegetables, mushrooms, and ornamentals such as cut flowers during storage and transportation. Such treatment can also be used for biological and microbial decontamination as well as pesticide remediation or pathogen decontamination. More particularly, the present invention relates to a device and method for the provision of antimicrobial activity and moisture protection for treatment of an enclosed or partially enclosed space such as where such goods are contained within storage spaces (e.g., package, refrigerator, cold room, or shipping container). The present invention also relates to a device and method for disinfecting and maintaining appropriate moisture levels for item such as food storage and handling areas, food containers and food preparation implements.

BACKGROUND OF THE INVENTION

In many cases of stored or transported goods, the presence of water is detrimental and desiccant materials such as silica gels or clays are often placed in the shipping containers or inside individual packages within the shipping containers to reduce the dew point. While this is advantageous for most transported goods, it is not beneficial for produce such as fruits, vegetables, mushrooms, ornamentals such as cut flowers, and in general all living things, which require water to extend the quality and shelf life of the products.

The addition of water to produce is not easily done and, in some cases, impossible during storage or transportation. Harvested crops (e.g., fruits, vegetables, and mushrooms) and cut plants (e.g., ornamentals such as flowers, etc.) will quickly dehydrate when in storage and/or packed for transportation and distribution. Keeping high moisture levels is important for freshness but addition of water to products during storage can be problematic as it has a tendency to increase the potential for degradation by microbes, fungi, bacteria and other unwanted or toxic organisms living and developing in environments with high moisture. This is particularly an issue with soft or delicate produce such as strawberries or raspberries.

Microbial contamination of such goods can have significant detrimental impacts on those goods, particularly in transportation and/or storage. Approaches to preventing microbial activity have involved the reduction of moisture, disinfection of the goods or items, or the prolonged or continuous application of an antimicrobial agent while the goods or items are in storage.

Previously, it has been disclosed that an approach to preventing microbial damage or spoilage of goods and other items contained within a confined storage space or handling area, can involve the creation of an equilibrium concentration of a suitable chemical disinfectant vapor such as hydrogen peroxide vapor and/or peracetic acid (PAA) vapor. Such hydrogen peroxide and/or PAA vapors or gas can be generated by different means such as equipment or devices but also various chemicals generating means such gas or vapors in situ. For example, PAA can be formed from tetraacetylethylenediamine (TAED) and sodium percarbonate. This approach offers the advantage of continuous application of a suitable chemical disinfectant vapor whereby microbial growth within the space may be reduced. However, while excellent results have been achieved, some limitations to the application and/or effectiveness of this approach are the need to employ liquid chemical solutions (e.g., hydrogen peroxide solutions and/or PAA solutions) which may have a relatively short shelf-life and require precautions to be taken to prevent both the user from coming into contact with the solutions and the solutions from contacting the stored goods. It has also been noted that the relative humidity within the storage space may have a considerable impact on the efficacy of the approach.

Hydrogen peroxide and/or PAA gas or vapor in the presence of sufficient water vapor helps minimize food decay, enhances freshness and increases shelf life and appearance by providing a disinfection mean of the surrounding air.

It is known in the art that hydrogen peroxide and/or peracetic acid (PAA) in the form of a vapor can be used as an antimicrobial or biocidal agent in a confined space or area and thus in many applications. Hydrogen peroxide is a well-known compound (the Merck Index Thirteenth Edition, p 858-859) available commercially in various concentrations up to 70%. Hydrogen peroxide in the form of a liquid or a vapor can be used to sanitize products mostly by oxidation in enclosed spaces and is used to this effect in many industries (e.g., food packaging, medical equipment). Similarly, PAA is a well-known chemical (the Merck Index Thirteenth Edition, p 1283) often used in the process of produce sanitization.

The presence of hydrogen peroxide and/or PAA also helps reducing ethylene gas produced by living plants. Ethylene is a naturally occurring plant growth substance that has numerous effects on the growth, development and storage life of many fruits, vegetables and ornamental crops. It should be noted that many so-called detrimental effects of ethylene are simply responses that are unwanted in certain situations, but which are beneficial in others. Exposure may occur in storage or transit from ethylene produced by the crop itself or adjacent crops. Ethylene gas speeds up the ripening process of ethylene sensitive produce and the reduction of its level is often essential to keep products fresh.

WO 2015/139075 discloses a device that provides hydrogen peroxide to a closed storage environment but at the same time removes water vapor, as water is needed to induce the reaction within the device to release hydrogen peroxide. While the presence of hydrogen peroxide can be helpful in reducing microbial count, reducing the amount of water is counterproductive in situations where water is essential to keep stored produce in optimal conditions of freshness. Accordingly, reducing water content in containers with produce is perceived as negatively impacting the produce freshness.

WO 2016/176486 describes a method to inhibit ethylene using non-hydrated purified hydrogen peroxide gas (PHPG)

that is free of ozone, plasma species or organic species. It discloses that hydrogen peroxide aerosols and vapors prepared from aqueous solutions of hydrogen peroxide differ from PHPG.

WO 2014/86805 describes a method to control arthropods, including insects and arachnids using non-hydrated purified hydrogen peroxide gas (PHPG) that is free of ozone, plasma species or organic species. It discloses that hydrogen peroxide aerosols and vapors prepared from aqueous solutions of hydrogen peroxide differ from PHPG.

WO 2019/067232 describes a peroxide and water delivery system produced by combining a liquid peroxide (e.g., hydrogen peroxide, PAA and possibly other ingredients such as alcohols) and water with an inorganic solid support such as silica.

Contrary to the disclosure of WO 2016/176486 and WO 2014/86805, which indicates that hydrogen peroxide issued from an aqueous solution is not suitable in occupied space, or WO 2015/139075, which discloses a method where water levels in a storage/shipping container are reduced in order to be able to generate hydrogen peroxide, the present inventors discovered that a combination of low levels of hydrogen peroxide vapor in combination with water vapor in order to saturate the environment or air surrounding produce in a package or container creates an enhanced environment which helps conserve the produce in a state of freshness not achievable through the use of a suitable chemical disinfectant vapor or moisture control alone. In addition, or as an alternative, to treating the environment or air surrounding produce in a package or container that creates an enhanced environment and helps conserve the produce, the present invention is also effective in treating surfaces within such containers or other enclosed or partially enclosed space. The device and method of the present invention shows an unexpected benefit by increasing water saturation in the presence of hydrogen peroxide vapor in closed or partially closed spaces such as containers, boxes or packaging shells.

Water absorbing resins or matrices can vary in shape and in composition and are particularly well known in the industry for hygiene products such as diapers, sanitary goods, spill control, waste solidification, wiping cloth, and the likes. Such materials can include super absorbent polymers (SAP), hydrogels water crystals or cross-linked polyacrylates and typically are lightly cross-linked. Water absorbing matrices also include inorganic solid supports such as silica, which can be precipitated or fumed.

The present inventors discovered that such matrices would act as a reservoir for hydrogen peroxide solutions or peracetic acid generating solutions and water and that the absorbed product would remain stable and available for release under appropriate conditions. In the case of a passive release in air, the amount of vapor or gas present in the surrounding volume will be mostly driven by the vapor pressure of the compounds at a given temperature. The liquid-vapor phase relationship for hydrogen peroxide is well-known and extensively described in the book "Hydrogen Peroxide" by Schumb et al. published in 1955 (p 222-229).

SUMMARY OF THE INVENTION

In a first aspect, the present invention relates to a device that releases both water vapor and an antimicrobial vapor material into an enclosed or partially enclosed space or area. The water and antimicrobial vapor may be released through a permeable container or barrier enclosing a matrix into which the water and an antimicrobial vapor producing material are absorbed or adsorbed.

In a second aspect, the present invention provides a method to prevent microbial degradation or spoilage and dehydration of goods and other items contained within an enclosed or partially enclosed space or storage area. The method comprises providing a device comprising a container which houses a matrix that holds both water and an antimicrobial vapor-generating material, in an arrangement such that in an enclosed or partially enclosed space or area both water vapor and the antimicrobial vapor are released into the enclosed or partially enclosed space or area through a permeable barrier.

In a third aspect, the present invention provides a method or device to disinfect, remove toxins such as pesticides, chemical biologicals or warfare agent gas such as sulfur gas (aka mustard gas) from an enclosed or partially enclosed space or area and/or the surfaces therein.

DETAILED DESCRIPTION OF THE INVENTION

In one aspect, the present invention is directed towards a passive device that simultaneously dispenses an antimicrobial vapor such as hydrogen peroxide vapor and/or peracetic acid (PAA) vapor and water vapor through a permeable barrier from an absorptive or adsorptive matrix. The matrices can be composed of an inorganic support such as silica including but not limited to precipitated silica or fumed silica. The matrix can be composed of super absorbent polymers (SAP) in a form of a gel, granular form, compacted form, bead gel form, powder or fiber. Other types of matrices can be composed of an organic support such as polyvinylpyrrolidone PVP (e.g., Peroxydone™ complexes available from Ashland Global Specialty Chemicals Inc.).

By super absorbent polymer, or SAP, is meant a polymeric material that absorbs at least 10 times its own dry weight in fluid and that retains the absorbed fluid under moderate pressure. The absorbed fluid is taken into the SAP rather than being contained in macroscopic pores from which the fluid could be eliminated by squeezing. Examples of SAPs include, but are not limited to acrylate and methacrylate polymers.

The antimicrobial vapor is generated from a material or materials capable of generating an antimicrobial vapor such as hydrogen peroxide vapor and/or peracetic acid (PAA) vapor.

Peracetic acid can be formed in situ such as from tetraacetylethylenediamine (TAED) and sodium percarbonate or hydrogen peroxide. For the purposes of the present invention, an antimicrobial vapor is regarded as being vapor, which in air results in a reduction in the viable population (cfu; colony forming units) of microorganisms such as *Pseudomonas aeruginosa*.

The device of the present invention releases an antimicrobial vapor such as hydrogen peroxide vapor along with water vapor through a permeable barrier based on Raoult's law of vapor equilibrium in an enclosed space. The matrices containing the water and material or materials capable of generating an antimicrobial vapor such as hydrogen peroxide vapor are physically contained or separated from the produce or other material in the enclosed area such as in a container having a permeable barrier or a container of permeable material, which is permeable to both water vapor and an antimicrobial vapor such as hydrogen peroxide vapor. The permeable barrier can be composed of woven or non-woven fibers, which may be open mesh, made of high-density polyethylene (HDPE) fibers such as Tyvek®, GoreTex® membranes made of polytetrafluoroethylene (PTFE) (available from W. L. Gore & Associates), or membranes made of material allowing the hydrogen peroxide vapor and water vapor to diffuse through it such as Pebax® films (available from Arkema Inc.) or other similar products, or mesh like woven or non-woven products that would keep a separating space between the absorptive matrix and the produce treated. The device can be in the form of a sachet, strip, pad or any shape or form.

Sachets, strips, or pads can be kept in bulk within a sealed container (impermeable bag or pouch such as a LDPE bag, metalized foil, bucket or similar container) and used as needed without having to activate the device or removing any barrier to activate the device. The release is triggered by the natural evaporation of the antimicrobial vapor such as hydrogen peroxide and water from the matrix into the closed space.

The release of the antimicrobial vapor such as hydrogen peroxide vapor and/or peracetic acid (PAA) vapor and water vapor in the present invention does not require any energy input (electric, light such as UV, heat, cold, etc.) or chemicals such as water (in the form of liquid or moisture) to trigger the release of antimicrobial vapor such as hydrogen peroxide vapor and water vapor in the volume or room (enclosed or partially enclosed space) to be treated.

The release rate of antimicrobial vapor such as hydrogen peroxide vapor and/or peracetic acid (PAA) vapor and water vapor is triggered by opening the impermeable barrier bag/package. The impermeable barrier bag/package surrounding the device acts as a barrier to the diffusion of the antimicrobial vapor such as hydrogen peroxide vapor and water vapor and prevents a premature release through the membrane or from the absorptive matrix. Once the impermeable barrier bag/package surrounding the device is open to the environment, antimicrobial vapor such as hydrogen peroxide vapor and/or peracetic acid (PAA) vapor and water vapor will diffuse through the device membrane from the matrix such as silica or SAP into the space to be treated. The space to be treated can be treated over minutes, hours, days or weeks depending on the device size and geometry, room size, relative humidity and temperature of the room.

The matrix in the device can be in the form of a gel, bead, granules, fiber pad or powder (e.g., antimicrobial such as hydrogen peroxide on a solid organic matrix such as PVP or an inorganic matrix such as silica). In this application, the SAP beads, gel or pads containing the antimicrobial such as hydrogen peroxide and water enclosed in a permeable barrier are inserted inside the closed space that is to be treated. Release of hydrogen peroxide vapor or peracetic acid vapor and water vapor through the permeable barrier is triggered and is the result of the equilibrium established between vapor phases in the space and the hydrogen peroxide liquid or peracetic forming materials and water trapped on the matrix. The beads, gel, solid or peroxide powder would be transported/handled in sealed container or package containing the hydrogen peroxide liquid or peracetic forming materials and water in the permeable barrier as described above which would be opened to begin the diffusion of the hydrogen peroxide vapor and water vapor through the permeable barrier into the space to be treated.

Applications for the device of the present invention, which is able to disinfect surfaces, goods and volumes, are varied. Disinfection for food related items is beneficial in packinghouses, transportation containers, processing facilities, distribution centers, retailers, and at home. Additionally, hospitals, veterinary clinics and pharmaceutical facilities have a demand for devices able to quickly, and with proven efficacy, disinfect surfaces, rooms, equipment and goods. There are also many military applications where a portable self-activating disinfection device, which is transportable in the field, would be valuable.

The release of an antimicrobial and water vapor by the devices of the present invention can be used in a wide variety of applications. The devices of the present invention can be used to disinfect an area such as medical facilities, animal and veterinary facilities, food storage areas, and food transportation containers by placing the devices of the present invention into such containers/areas. The devices of the present invention can be used to disinfect items such as facemasks and reusable medical supplies by exposing such items to be disinfected to the devices of the present invention in a closes container/area. The devices of the present invention can be used to control arthropods such as insects, arachnids, and myriapods in confined areas by placing the devices of the present invention in the confined area. The devices of the present invention can be used for treatment of parasites such as *Varroa* mites, trachea mites and other pests present in or for disinfection of beehives by placing the device of the present invention into a beehive to be treated. The devices of the present invention can be used for the detoxification of military biological and warfare agents by exposing contaminated items to the devices in an enclosed area. The devices of the present invention may also be used for the remediation of pesticide contamination on objects, walls, surfaces, rooms, storage rooms, etc. by placing the devices of the present invention in the contaminated area.

While it is possible to fog or mist hydrogen peroxide, such applications are targeted at achieving high hydrogen peroxide concentration, which are not compatible in spaces where direct contact with users and consumers is possible. According to the American Conference of Governmental Industrial Hygienists (ACGIH), hydrogen peroxide vapor concentration (from any source) are considered toxic when concentration exceed 1.4 mg/kg air or 1 ppm. The ACGIH states that excursions in worker exposure levels may exceed 3 times the TLV-TWA for no more than a total of 30 minutes during a workday, and under no circumstances should they exceed 5 times the TLV-TWA, provided that the TLV-TWA is not exceeded. (TLV=threshold limit value and TWA=Time-Weighted Average). [2008 TLVs and BEIs based on the Documentation of the threshold Limit Values for Chemical Substances and Physical Agents and Biological Exposure Indices, p 5.]

The ACGIG TLV for hydrogen peroxide is 1 ppm, 8 hour TWA, and thus, according to the ACGIH, the maximum exposure to hydrogen peroxide should be no more than 5 ppm. Some states, Washington and Hawaii have Short Term Exposures (STELs) for hydrogen peroxide of 3 ppm as do some other countries such as the United Kingdom and some other countries (STEL=2 ppm) [Ref. EH40/2005 Workplace exposure limits 2005]. While there is no OSHA STEL for hydrogen peroxide, this ACGIH guidance represents best practice when using hydrogen peroxide.

The antimicrobial hydrogen peroxide vapor and/or peracetic acid vapor concentrations achieved by passive evaporation in enclosed or partially enclosed spaces provided by the present invention can vary between about 0.01 ppm and about 1500 ppm, preferably between about 0.01 ppm and about 1000 ppm, more preferably between about 0.05 ppm and about 400 ppm, even more preferably between about 0.05 ppm and about 100 ppm and even more preferably between about 0.05 ppm and 50 ppm. In the cases where a direct and sustained contact with users is possible, the hydrogen peroxide vapor concentration would be between about 0.01 ppm and about 15 ppm, preferably between 0.01 ppm and 5 ppm and more preferably between 0.01 ppm and 1 ppm. Such hydrogen peroxide vapor concentrations can be generated by hydrogen peroxide generating material concentration in the absorbent matrix of from about 0.01% to about 50% (w/w), preferably between 0.1% and 35% and more preferably between 0.1% and 10%; and in an inorganic matrix such as silica from about 0.01% to about 70% (w/w), preferably between 0.1% and 50%.

The level of hydrogen peroxide vapor dispensed by the device of the present invention is safe to the user or consumer as the amount of hydrogen peroxide in direct contact with the user from handling the product will be well below 1 ppm. Similarly, large storage or handling areas are vented and the level of hydrogen peroxide vapor are expected to be well below the TWA limit of 1 ppm. The potentially higher level of hydrogen peroxide found inside closed spaces containing produce would be diluted many fold by incoming ambient air when opening the closed container resulting in hydrogen peroxide concentration well below 1 ppm.

Produce (e.g., fruits, vegetables, mushrooms, or cut flowers) in a closed container treated with a device of the present invention that releases both water vapor and antimicrobial such as hydrogen peroxide vapor showed a storage life and freshness that was extended for several days with minimal produce decay and beneficial appearance to the customer.

Hydrogen peroxide as a vapor is an excellent biocidal agent. Sporicidal efficiency of chemical decontamination agents is often expressed as the D-value, which represents the time (minutes) necessary to kill 90% of the starting amount of microorganisms (or logarithms of the amount) at a constant temperature. The table below [Compilation of available data on building decontamination alternatives, EPA/600/R-05/036, March 2005] reports D-value data of experiments conducted with hydrogen peroxide in liquid and vapor phase.

| | D-value [min] | |
| --- | --- | --- |
| Tested microorganism (Spores) | Liquid solution of $H_2O_2$ $c(H_2O_2) = 370$ mg $l^{-1}$ $T = 24\text{-}25°$ C. | VPHP $c(H_2O_2) = 1\text{-}2$ mg $l^{-1}$ $T = 24\text{-}25°$ C. |
| Bacillus | 1.5 | 1-2 |
| Bacillus subtilis | 2.0-7.3 | 0.5-1 |
| Clostridium sporogenes | 0.8 | 0.5-1 |

U.S. Environmental Protection Agency. (2005). Compilation of Available Data on Building Decontamination Alternatives. EPA/600/R-05/036. Cincinnati, Ohio These results show that, in order to kill selected microorganisms, a solution of hydrogen peroxide 200 times more concentrated than a vapor phase is necessary to get comparable D-value results. Accordingly, in many applications, vapor decontamination is preferred.

Aspect 1. A chemical dispensing device, comprising (a) an absorbent matrix, (b) water absorbed onto said absorbent matrix and (c) an antimicrobial vapor generating material absorbed onto said absorbent matrix, (d) enclosed within a barrier system, at least a portion of which is permeable to antimicrobial vapor and water vapor, wherein said chemical dispensing device releases water vapor and antimicrobial vapor when exposed to the atmosphere.

Aspect 2. The chemical dispensing device of aspect 1, wherein the absorbent matrix comprises a super absorbent polymer.

Aspect 3. The chemical dispensing device of aspect 2, wherein said super absorbent polymer comprising a cross-linked polymer.

Aspect 4. The chemical dispensing device of aspect 1, wherein said absorbent matrix comprises polyvinylpyrrolidone.

Aspect 5. The chemical dispensing device in aspect 1, wherein said absorbent matrix comprises an inorganic silica matrix selected from the group consisting of precipitated silica and fumed silica.

Aspect 6. The chemical dispensing device of aspect 1 to 5, wherein said absorbent matrix is in a form selected from the group consisting of solid, granule, powder, and fiber.

Aspect 7. The chemical dispensing device of aspect 1 to 6, wherein said barrier system comprises a sachet.

Aspect 8. The chemical dispensing device of aspects 1 to 6, wherein said barrier system comprises a pad.

Aspect 9. The chemical dispensing device of aspects 1 to 8, wherein said portion permeable to said antimicrobial vapor and water vapor comprises a mesh fabric.

Aspect 10. The chemical dispensing device of aspects 1 to 8, wherein said portion permeable to antimicrobial vapor and water vapor comprises a woven or a non-woven, high-density polyethylene fiber or polytetrafluoroethylene fiber.

Aspect 11. The chemical dispensing device of aspects 1 to 8, wherein said portion permeable to antimicrobial vapor and water vapor comprises a spunbond non-woven.

Aspect 12. The chemical dispensing device of aspects 1 to 8, wherein said portion permeable to said antimicrobial vapor and water vapor comprises a polymeric film.

Aspect 13. The chemical dispensing device of aspects 1 to 12, wherein the antimicrobial vapor generating material concentration on the absorbent matrix varies from about 0.01% to about 70% (w/w).

Aspect 14. The chemical dispensing device of aspects 1 to 13 wherein said antimicrobial vapor generating material is hydrogen peroxide.

Aspect 15. The chemical dispensing device of aspects 1 to 13 wherein said antimicrobial vapor generating material is peracetic acid.

Aspect 16. The chemical dispensing device of aspects 1 to 15 wherein said antimicrobial vapor generating material contains 0.1 to 20% (w/w) alcohol.

Aspect 17. The chemical dispensing device of aspects 1 to 15 wherein said antimicrobial vapor generating material contains 0.1 to 20% (w/w) essential oils.

Aspect 18. A method of both sanitizing and humidifying an enclosed or partially enclosed space comprising providing said space with an antimicrobial in vapor phase and water in vapor phase generated by passive evaporation of both an antimicrobial vapor and water vapor from an absorbent matrix enclosed within a barrier system, at least a portion of which is permeable to antimicrobial vapor and water vapor.

Aspect 19. The method according to aspect 18 wherein said absorbent matrix comprises a super absorbent polymer.

Aspect 20. The method according to aspect 18, wherein said absorbent matrix comprises polyvinylpyrrolidone.

Aspect 21. The method according to aspect 18, wherein said absorbent matrix comprises an inorganic silica matrix selected from the group consisting of precipitated silica and fumed silica.

Aspect 22. The method according to aspect 18 to 21, wherein said absorbent matrix is in a form selected from the group consisting of solid, granule, powder, and fiber.

Aspect 23. The method according to aspects 18 to 22, wherein said barrier system comprises a sachet.

Aspect 24. The method according to aspects 18 to 22, wherein said barrier system comprises a pad.

Aspect 25. The method according to aspects 18 to 24, wherein the concentration of antimicrobial vapor generated in said enclosed or partially enclosed space varies from about 0.01 ppm to 1500 ppm in concentration.

Aspect 26. The method according to aspects 18 to 25 wherein said antimicrobial vapor is hydrogen peroxide vapor generated from a solution of hydrogen peroxide absorbed on said absorbent matrix.

Aspect 27. The method according to aspects 18 to 25 wherein said antimicrobial vapor is peracetic acid vapor generated in situ from a solution absorbed on said absorbent matrix.

Example 1: Release of Hydrogen Peroxide on SAP at Room Temperature in an Open Environment Five beads of SAP loaded with various concentrations of hydrogen peroxide were set to dry in an open environment at room temperature. A dry SAP bead weighs around 0.022 g, but once loaded with liquid, a bead weighed 2.2081 g (5% $H_2O_2$ solution), 1.8595 g (10% $H_2O_2$ solution) and 1.5994 g (15% $H_2O_2$ solution), respectively.

TABLE 1

| 5 beads each | Concentration | start | 1 hour | 2 hour | 3 hour | 4 hour | 5 hour | 24 hour |
|---|---|---|---|---|---|---|---|---|
| | | | Beads weight and cumulated loss at RT in an open environment | | | | | |
| Average in g | 5% | 10.1660 | 9.7890 | 9.5607 | 9.2394 | 9.0229 | 8.6773 | 4.5909 |
| Cumulated loss in % | 5% | 0.0000 | 3.7084 | 5.9537 | 9.1147 | 11.2444 | 14.6434 | 54.8403 |
| Average in g | 10% | 9.2939 | 8.9300 | 8.6933 | 8.3470 | 8.1155 | 7.8018 | 3.9830 |
| Cumulated loss in % | 10% | 0.0000 | 3.9160 | 6.4628 | 10.1884 | 12.6798 | 16.0546 | 57.1437 |
| Average in g | 15% | 7.4500 | 7.1475 | 6.9532 | 6.6626 | 6.4534 | 6.1815 | 3.0499 |
| Cumulated loss in % | 15% | 0.0000 | 4.0611 | 6.6691 | 10.5698 | 13.3778 | 17.0268 | 59.0622 |

Example 2: Release Rate in Cold Enclosed Environment (a) A non-woven mesh bag allowing air exchanges containing ten SAP beads loaded with 8% $H_2O_2$ solution (10 beads weight: 24 g) was placed in a non-vented refrigerator. Temperature of the refrigerator was set at 5° C. Volume of the refrigerator: 7.9 cuft or 0.224 m$^3$. Concentration of hydrogen peroxide was measured in the air using a C16 PortaSens II sensor. Concentrations of hydrogen peroxides were measured in ppm at the top and bottom of the refrigerator. A slow release of hydrogen peroxide gas was observed over a period of 39 days.

TABLE 2

| time in | Concentration $H_2O_2$ in Air (ppm) | |
|---|---|---|
| days | Bottom | Top |
| 0 | 0.0 | 0.0 |
| 3 | 0.9 | 0.9 |
| 4 | 0.9 | 0.9 |
| 5 | 1.0 | 1.0 |
| 7 | 1.7 | 1.7 |
| 11 | 3.5 | 3.5 |
| 12 | 3.4 | 3.6 |
| 13 | 3.4 | 3.8 |
| 14 | 3.9 | 3.3 |
| 17 | 3.5 | 3.2 |
| 21 | 2.9 | 2.8 |
| 25 | 2.1 | 2.3 |
| 28 | 1.8 | 1.6 |

TABLE 2-continued

| time in | Concentration $H_2O_2$ in Air (ppm) | |
|---|---|---|
| days | Bottom | Top |
| 34 | 0.8 | 0.8 |
| 35 | 0.6 | 0.6 |
| 39 | 0.0 | 0.0 |

(b) Hydrogen peroxide released was measured in a refrigerator set at a typical cold temperature (T=5.1-5.2° C.) over a period of 47 days. Volume of refrigerator: 224 liters. Sachet size: 50.0 g of solid hydrogen peroxide (hydrogen peroxide on silica) at a concentration of 35%. The release of hydrogen peroxide was constant and sustained over at least 30 days.

| Time | $H_2O_2$ Concentration in Air (ppm) |
|---|---|
| 0 (1 hour) | 1.6 |
| 5 days | 7.2 |
| 7 days | 7.2 |
| 12 days | 7.1 |

-continued

| Time | $H_2O_2$ Concentration in Air (ppm) |
|---|---|
| 14 days | 6.7 |
| 19 days | 7.3 |
| 21 days | 7.8 |
| 22 days | 7.9 |
| 29 days | 7.5 |
| 34 days | 4.53 |
| 35 days | 4.2 |
| 36 days | 4.15 |
| 39 days | 2.85 |
| 43 days | 1.8 |
| 47 days | 1.3 |

Example 3: Release Rate in a Small Enclosed Space

Release of hydrogen peroxide was measured using a PortaSens detector (Portable Gas Leak Detector, Analytical Technology, Inc.) in a Styrofoam box with a volume V=13.2 liters (T=21° C., RH=75%). The results are provided in ppm of hydrogen peroxide in air. Small sachets (dimension: 4.8 cm×5.6 cm) having a surface area of 53.76 cm$^2$ (includes both sides) are introduced in the box and the concentration of $H_2O_2$ followed over time. The sachet contains approximately 5.0 g of 35% hydrogen peroxide powder (hydrogen peroxide on silica). Table 3 shows the recorded concentrations in ppm of $H_2O_2$ in the box over time for 1 and 3 sachets. A sustain and relatively constant release was observed over a period of 7 days.

TABLE 3

| Time | Type | H$_2$O$_2$ Concentration in Air (ppm) |
|---|---|---|
| 0 (30 min) | 1 × Small (5 g) | 42.0 |
| 6 days | 1 × Small (5 g) | 41.9 |
| 8 days | 1 × Small (5 g) | 30.9 |
| 13 days | 1 × Small (5 g) | 0.0 |
| 0 (1 hour) | 3 × Small (3 × 5 g) | 73.8 |
| 0 (2 hours) | 3 × Small (3 × 5 g) | 99.5 |
| 5 days | 3 × Small (3 × 5 g) | 79.6 |
| 7 days | 3 × Small (3 × 5 g) | 47.8 |
| 12 days | 3 × Small (5 g) | 0.7 |

Example 4: Release Rate in a Small Enclosed Space

The use of a larger sachet containing 50 g of powder at 35% hydrogen peroxide (hydrogen peroxide on silica) in the same box as Example 3 (V=13.2 L) led to concentrations in hydrogen peroxide over 120 ppm (over the instrument sensor upper limit). Sachet dimensions: 17.7×12.5 cm; total surface area (both sides): 442.5 cm$^2$. See results for the concentration measured in the first hour in the Table 4.

TABLE 4

| Time | Type | H$_2$O$_2$ Concentration in Air | Sachet Weight |
|---|---|---|---|
| 1 hour | 1 × large | >120 | 50.17 gm |

Example 5: Release Rate in a Small Enclosed Space

A similar experiment conducted in the same box as Examples 3 and 4 with a small sachet containing 10 g of solid powder with a 35% concentration in hydrogen peroxide. Hydrogen peroxide concentrations over time inside the box are reported in the Table 5. The data shows a sustained stable and constant release over a period of 25 days

TABLE 5

| Time (Days) | Type | H$_2$O$_2$ Concentration in Air (ppm) |
|---|---|---|
| 0 | 1 × Small (10 g) | 79.8 |
| 1 | 1 × Small (10 g) | 99.1 |
| 7 | 1 × Small (10 g) | 68.0 |
| 13 | 1 × Small (10 g) | 68.7 |
| 14 | 1 × Small (10 g) | 69.4 |
| 15 | 1 × Small (10 g) | 68.6 |
| 19 | 1 × Small (10 g) | 67.1 |
| 22 | 1 × Small (10 g) | 59.1 |
| 26 | 1 × Small (10 g) | 50.5 |
| 28 | 1 × Small (10 g) | 31.5 |
| 33 | 1 × Small (10 g) | 0.6 |

Examples 6: Effect on Biological Indicators

Efficacy of the treatment was validated with a biological indicator: *Geobacillus stearothermophilus* (1.9×106 CFU per stainless steel carrier). The D-value: 0.8 min in 2 mg/L gaseous H$_2$O$_2$. After treatment, the indicator carriers were incubated in solutions at 55-60° C. for 7 days. After the incubation time, the color of the solution indicates the following:
Yellow=growth=non sterile
Purple=no growth=sterile The indicator left in the cooler size box of Example 3 for a period of two days (with 1 small sachet) showed that the inside of the box was sterile (purple color) compared to controls left outside the box (yellow color).

Having described the invention, we now claim the following and their equivalents.

The invention claimed is:

1. A chemical dispensing device, comprising (a) an absorbent matrix, (b) water absorbed onto said absorbent matrix and (c) an antimicrobial vapor generating material absorbed onto said absorbent matrix, (d) enclosed within a barrier system, wherein at least a portion of the barrier system is permeable to antimicrobial vapor and water vapor,
wherein said chemical dispensing device releases water vapor and antimicrobial vapor when exposed to the atmosphere,
wherein said antimicrobial vapor generating material is hydrogen peroxide, peracetic acid or a combination thereof.

2. The chemical dispensing device of claim 1, wherein the absorbent matrix comprises a super absorbent polymer.

3. The chemical dispensing device of claim 2, wherein said super absorbent polymer comprising a cross-linked polymer.

4. The chemical dispensing device of claim 1, wherein said absorbent matrix comprises polyvinylpyrrolidone.

5. The chemical dispensing device in aspect 1, wherein said absorbent matrix comprises an inorganic silica matrix selected from the group consisting of precipitated silica and fumed silica.

6. The chemical dispensing device of claim 1, wherein said absorbent matrix is in a form selected from the group consisting of solid, granule, powder, and fiber.

7. The chemical dispensing device of claim 1, wherein said barrier system comprises a sachet.

8. The chemical dispensing device of claim 1, wherein said barrier system comprises a pad.

9. The chemical dispensing device of claim 1, wherein said portion permeable to said antimicrobial vapor and water vapor comprises a mesh fabric.

10. The chemical dispensing device of claims 1, wherein said portion permeable to antimicrobial vapor and water vapor comprises a woven or non-woven, high-density polyethylene fiber or polytetrafluoroethylene fiber.

11. The chemical dispensing device of claim 1, wherein said portion permeable to antimicrobial vapor and water vapor comprises a spunbond non-woven.

12. The chemical dispensing device of claim 1, wherein said portion permeable to said antimicrobial vapor and water vapor comprises a polymeric film.

13. The chemical dispensing device of claim 1, wherein the antimicrobial vapor generating material concentration on said absorbent matrix varies from about 0.01% to about 70% (w/w).

14. The chemical dispensing device of claim 1, wherein said said absorbent matrix further comprises a solution absorbed thereon and said peracetic acid is a peracetic acid vapor generated in situ from the solution.

15. The chemical dispensing device of claim 14, wherein the solution comprises tetraacetylethylenediamine (TAED) and at least one of sodium percarbonate or hydrogen peroxide.

16. The chemical dispensing device of claim 1, wherein said antimicrobial vapor generating material contains 0.1 to 20% (w/w) alcohol.

17. The chemical dispensing device of claim 1, wherein said antimicrobial vapor generating material contains 0.1 to 20% essential oils.

18. A method of both sanitizing and humidifying an enclosed or partially enclosed space comprising providing said space with an antimicrobial in vapor phase and water in vapor phase generated by passive evaporation of both an antimicrobial vapor and water vapor from an absorbent matrix enclosed within a barrier system, wherein at least a portion of the barrier system is permeable to antimicrobial vapor and water vapor, wherein said antimicrobial vapor generating material is hydrogen peroxide, peracetic acid or a combination thereof.

19. The method according to claim 18, wherein said absorbent matrix comprises a super absorbent polymer.

20. The method according to claim 18, wherein said absorbent matrix comprises polyvinylpyrrolidone.

21. The method according to claim 18, wherein said absorbent matrix comprises an inorganic silica matrix selected from the group consisting of precipitated silica and fumed silica.

22. The method according to claim 18, wherein said absorbent matrix is in a form selected from the group consisting of solid, granule, powder, and fiber.

23. The method according to of claim 18, wherein said barrier system comprises a sachet.

24. The method according to of claim 18, wherein said barrier system comprises a pad.

25. The method according to claim 18, wherein the concentration of antimicrobial vapor generated in said enclosed or partially enclosed space varies from about 0.01ppm to 1500 ppm in concentration.

26. The method according to claim 18, wherein said hydrogen peroxide is a hydrogen peroxide vapor generated from a solution of hydrogen peroxide absorbed on said absorbent matrix.

27. The method according to claim 18, wherein said peracetic acid vapor is a peracetic acid vapor generated in situ from a solution absorbed on said absorbent matrix, and wherein the solution comprises tetraacetylethylenediamine (TAED) and at least one of sodium percarbonate or hydrogen peroxide.

\* \* \* \* \*